US00PP27726P3

(12) United States Plant Patent
Miyazaki

(10) Patent No.: US PP27,726 P3
(45) Date of Patent: Feb. 28, 2017

(54) ***PETUNIA* PLANT NAMED 'SUNSURF MIYARONA'**

(50) Latin Name: *Petunia×hybrida*
Varietal Denomination: Sunsurf Miyarona

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 96 days.

(21) Appl. No.: 14/545,192

(22) Filed: Apr. 4, 2015

(65) Prior Publication Data

US 2016/0295784 P1 Oct. 6, 2016

(51) Int. Cl.
*A01H 5/02* (2006.01)

(52) U.S. Cl.
USPC ..... Plt./356.12

(58) Field of Classification Search
USPC ..... Plt./356.1, 356.12
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Petunia* plant named 'Sunsurf Miyarona', characterized by its relatively compact, upright and mounding plant habit; vigorous growth habit; freely branching habit; freely flowering habit; long flowering period; double-type flowers that are deep salmon pink in color; and good garden performance and high temperature tolerance.

1 Drawing Sheet

Botanical designation: *Petunia×hybrida.*
Cultivar denomination: 'SUNSURF MIYARONA'.

BACKGROUND OF THE INVENTION

The present invention relates to a new and distinct cultivar of *Petunia* plant, botanically known as *Petunia×hybrida* and hereinafter referred to by the name 'Sunsurf Miyarona'.

The new *Petunia* plant is a product of a planned breeding program conducted by the Inventor in Higashiomi, Shiga, Japan. The objective of the breeding program is to create new compact and freely-flowering *Petunia* plants with double-type flowers and high temperature tolerance.

The new *Petunia* plant originated from a cross-pollination made by the Inventor in July, 2011 in Higashiomi, Shiga, Japan of a proprietary selection of *Petunia×hybrida* identified as code designation 11 Pet-42, not patented, as the female, or seed, parent with a proprietary selection of *Petunia×hybrida* identified as code designation 2588, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2012.

Asexual reproduction of the new *Petunia* plant by terminal cuttings in a controlled greenhouse environment in Higashiomi, Shiga, Japan since June, 2012 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Miyarona'. These characteristics in combination distinguish 'Sunsurf Miyarona' as a new and distinct *Petunia* plant:

1. Relatively compact, upright and mounding plant habit.
2. Vigorous growth habit.
3. Freely branching habit.
4. Freely flowering habit.
5. Long flowering period.
6. Double-type flowers that are deep salmon pink in color.
7. Good garden performance and high temperature tolerance.

Plants of the new *Petunia* can be compared to plants of the female parent selection. Plants of the new *Petunia* differ primarily from plants of the female parent selection in flower size as plants of the new *Petunia* have smaller flowers than plants of the female parent selection.

Plants of the new *Petunia* can be compared to plants of the male parent selection. Plants of the new *Petunia* differ primarily from plants of the male parent selection in plant habit as plants of the new *Petunia* are more compact and more upright than plants of the male parent selection.

Plants of the new *Petunia* can also be compared to plants of the *Petunia×hybrida* 'Sundarose', disclosed in U.S. Plant Pat. No. 24,430. In side-by-side comparisons conducted in Higashiomi, Shiga, Japan, plants of the new *Petunia* and 'Sundarose' differed primarily in the following characteristics:

1. Plants of the new *Petunia* were more upright and larger than plants of 'Sundarose'.
2. Leaves of plants of the new *Petunia* were elliptic in shape whereas leaves of plants of 'Sundarose' were ovate in shape.
3. Plants of the new *Petunia* were more freely flowering than plants of 'Sundarose'.

4. Plants of the new *Petunia* and 'Sundarose' differed in flower color as plants of 'Sundarose' had flowers that were bright red purple in color.
5. Plants of the new *Petunia* had smaller sepals than plants of 'Sundarose'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Miyarona' grown in a container.

The photograph at the bottom of the sheet is a close-up view of a typical flowering plant of 'Sunsurf Miyarona'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six and seven months old when the description and photographs, respectively, were taken. In the following description, color references are made to The Royal Horticultural Society Colour Chart, 2007 Edition, except where general terms of ordinary dictionary significance are used.

Botanical classification: *Petunia×hybrida* 'Sunsurf Miyarona'.

Parentage:

*Female, or seed, parent*.—Proprietary selection of *Petunia×hybrida* identified as code designation 11 Pet-42, not patented.

*Male, or pollen, parent*.—Proprietary selection of *Petunia×hybrida* identified as code designation 2588, not patented.

Propagation:

*Type*.—By terminal cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; white in color.

*Rooting habit*.—Freely branching; dense.

Plant description:

*Plant form and growth habit*.—Relatively compact, upright and mounding plant habit; freely branching habit with numerous lateral branches developing per plant; pinching enhances lateral branch development; vigorous growth habit.

*Plant height*.—About 26 cm.

*Plant diameter*.—About 58 cm.

Lateral branch description:

*Length*.—About 29 cm.

*Diameter*.—About 1.8 mm.

*Internode length*.—About 1.9 cm.

*Strength*.—Strong, flexible.

*Aspect*.—Mostly upright to outwardly.

*Texture*.—Pubescent.

*Color*.—Close to 138A.

Leaf description:

*Arrangement*.—Alternate, simple.

*Length*.—About 3.2 cm.

*Width*.—About 1.7 cm.

*Shape*.—Elliptic.

*Apex*.—Narrowly acute.

*Base*.—Attenuate.

*Margin*.—Entire.

*Texture, upper and lower surfaces*.—Pubescent.

*Venation pattern*.—Pinnate; reticulate.

*Color*.—Developing and fully expanded leaves, upper surface: Close to 137C; venation, close to 138C. Developing and fully expanded leaves, lower surface: Close to 137D; venation, close to 138D.

*Petioles*.—Length: About 6.7 mm. Diameter: About 2 mm. Texture, upper and lower surfaces: Pubescent. Color, upper and lower surfaces: Close to 138C.

Flower description:

*Flower arrangement and habit*.—Double-type salverform flowers arising from upper leaf axils; freely flowering habit with usually about 107 flowers developing per plant during the flowering season; flowers face mostly upright to outwardly.

*Fragrance*.—None detected.

*Natural flowering season*.—Plants of the new *Petunia* initiate and develop flowers about seven weeks after planting; long flowering period, flowering commences naturally during the spring and plants flower continuously throughout the summer until late autumn in Japan.

*Flower longevity*.—Individual flowers last about seven to ten days on the plant; flowers persistent.

*Flower buds*.—Length: About 2.8 cm. Diameter: About 6.5 mm. Shape: Cylindrical. Color: Close to 77C.

*Flower diameter*.—About 4.1 cm.

*Flower length (depth)*.—About 3.4 cm.

*Throat diameter*.—About 1.1 cm.

*Tube diameter, base*.—About 2 cm.

*Tube length*.—About 2.9 cm.

*Corolla*.—Arrangement: About 15 petals fused at the base and opening into a flared trumpet. Petal length from throat: About 1.7 cm. Petal width: About 1.8 cm. Petal shape: Roughly spatulate. Petal apex: Mucronate. Petal margin: Entire; strongly undulate. Petal texture, upper and lower surfaces: Smooth, glabrous. Throat texture: Smooth, glabrous. Tube texture: Pubescent. Color: Petal, when opening, upper surface: Close to 47B. Petal, when opening, lower surface: Close to 65C. Petal, fully opened, upper surface: Close to 58C; towards the base, close to 63D; venation, close to 47A; colors becoming closer to 58A and 52B with development. Petal, fully opened, lower surface: Close to 62C; venation, close to 62C; color does not change with development. Throat: Close to 145D; venation, close to 138B. Tube: Close to 157B; venation, close to 157B.

*Calyx*.—Arrangement: One star-shaped calyx tube with five sepals in a single whorl and fused at the base. Sepal length: About 8.3 mm. Sepal width: About 1.7 mm. Sepal shape: Narrowly elliptic. Sepal apex: Acute. Sepal margin: Entire. Sepal texture, upper and lower surfaces: Pubescent. Color: Developing sepals, upper surface: Close to 143A. Developing sepals, lower surface: Close to 143B. Fully expanded sepals, upper surface: Close to 143A. Fully expanded sepals, lower surface: Close to 143C.

*Peduncles*.—Length: About 8.3 mm. Diameter: About 1.2 mm. Strength: Strong, flexible. Aspect: Outwardly. Texture: Pubescent. Color: Close to 144B.

*Reproductive organs*.—Stamens: Quantity per flower: Five. Stamen length: About 1.3 cm to 1.6 cm. Anther shape: Ellipsoidal. Anther size: About 1.3 mm by 2.3 mm. Anther color: Close to 155C. Pollen amount: Scarce. Pollen color: Close to NN155D. Pistils: Quantity per flower: One. Pistil length: About 1.5 cm. Style color: Close to 144C. Stigma shape: Transversely ellipsoidal. Stigma color: Close to 144A. Ovary color: Close to 144A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Miyarona' as illustrated and described.

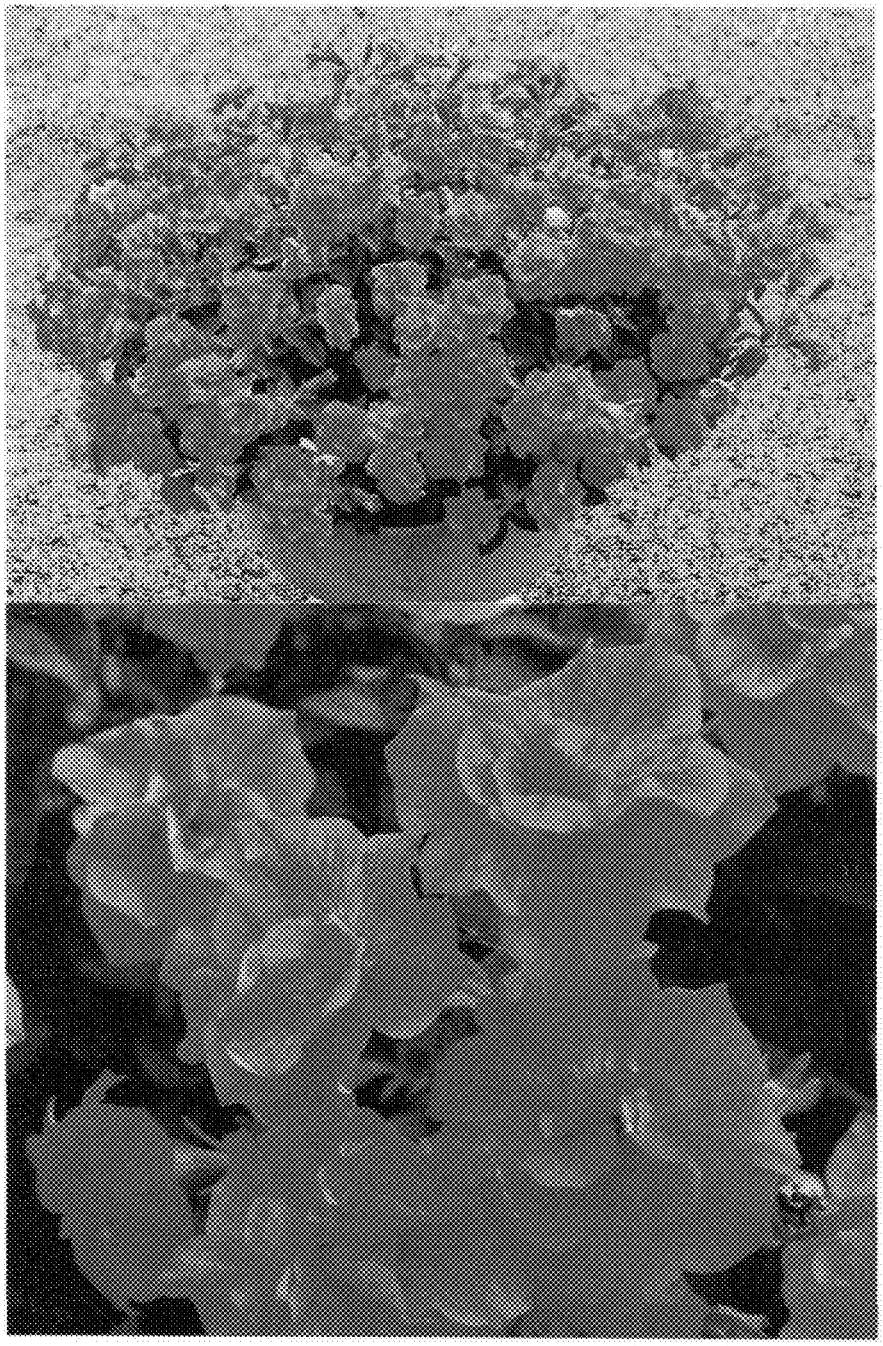

* * * * *